US007754456B2

(12) United States Patent  
Penttilä et al.

(10) Patent No.: US 7,754,456 B2  
(45) Date of Patent: Jul. 13, 2010

(54) PROCESS FOR PRODUCING ETHANOL

(75) Inventors: Merja Penttilä, Helsinki (FI); Matti Siika-Aho, Helsinki (FI); Jaana Uusitalo, Espoo (FI); Liisa Viikari, Helsinki (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 176 days.

(21) Appl. No.: 11/628,341

(22) PCT Filed: Jun. 6, 2005

(86) PCT No.: PCT/FI2005/000261

§ 371 (c)(1),  
(2), (4) Date: Dec. 19, 2006

(87) PCT Pub. No.: WO2005/118828

PCT Pub. Date: Dec. 15, 2005

(65) Prior Publication Data  
US 2008/0044877 A1 Feb. 21, 2008

(30) Foreign Application Priority Data  
Jun. 4, 2004 (FI) .................................. 20040775

(51) Int. Cl.  
*C12P 7/10* (2006.01)

(52) U.S. Cl. ..................................... 435/165

(58) Field of Classification Search ....................... None  
See application file for complete search history.

(56) References Cited

U.S. PATENT DOCUMENTS

| 6,090,595 | A | * | 7/2000 | Foody et al. | ................... | 435/99 |
| 7,109,005 | B2 | * | 9/2006 | Eroma et al. | ................ | 435/158 |
| 7,625,728 | B2 | * | 12/2009 | Eroma et al. | ................ | 435/158 |
| 2002/0164731 | A1 | * | 11/2002 | Eroma et al. | ................ | 435/163 |

OTHER PUBLICATIONS

Doran, J.B. et al., "Saccharification and fermentation of sugar cane bargasse by Klebsiella oxytoca P2 Containing chromosomally integrated genes encoding the Zymomonas mobilis ethanol pathway", Biotechnology and Bioengineering, 1994, p. 240-247, vol. 44.  
Stenberg, K. et al., "The influence of lactic acid formation on the simultaneous saccharification and Fermentation (SSF) of softwood to ethanol", Enzyme and Microbial Technology, 2000, p. 71-79, vol. 26.  
Söderström, J. et al., "Effect of washing on yield in one-and two step steam pretreatment of softwood For production of ethanol.", Biotechnology Progress, 2004, p. 744-749, vol. 20, No. 3.

Ollson, L. et al., "Fermentation of lignocellulosic hydrolysates for ethanol production.", Enzyme and Microbial Technology, Apr. 1996, p. 312-331, vol. 18.  
McMillan, J.D. et al., "Simultaneous saccharification and cofermentation of dilute-acid pretreated Yellow poplar hardwood to ethanol using xylose-fermenting Zymomonas mobilis.", Applied Biotechnology, 1999, p. 649-665, vol. 77-79.  
Wu, Z. et al., "Nonisothermal simultaneous saccharification and fermentation for direct conversion of Lignocellulosic biomass to ethanol.", Applied Biochemistry and Biotechnology, 1998, p. 479-492, vol. 70-72.  
Vincent S. Chang, et al.; "Fundamental Factors Affecting Biomass Enzymatic Reactivity", Applied Biochemistry and Biotechnology, vol. 84-86, 2000, p. 5-37.  
Teh-An Hsu; "Pretreatment of Biomass", Handbook on Bioethanol: Production and Utilization, Ed. C. E. Wyman, Chapter 10, p. 179-212 (1996).  
Priya Chandrakant, et al.; "Simultaneous Bioconversion of Cellulose and Hemicellulose to Ethanol", Critical Reviews in Biotechnology, 18(4): p. 295-331 (1998).  
C. S. Gong et al.; "Ethanol Production from Renewable Resources", Advances in Biochemical Engineering/Biotechnology, 1999, vol. 65, p. 207-241.  
Michael Kaylen, et al.; "Economic feasibility of producing ethanol from lignocellulosic feedstocks", Bioresource Technology 72 (2000), p. 19-32.  
Kerstin Steinberg, et al.; "Effect of Substrate and Cellulase Concentration on Simultaneous Saccharification and Fermentation of Steam-Pretreated Softwood for Ethanol Production", Biotechnology and Bioengineering, vol. 68, No. 2, Apr. 20, 2000, p. 204-210.  
Eva Palmgvist, et al.; "Design and Operation of a Bench-Scale Process Development Unit for the Production of Ethanol From Lignocellulosics", Bioresource Technology 58 (1996), p. 171-179.  
J. Saddler, et al.; "Steam pre-treatment of lignocellulosic residues", Forest Products Biotechnology, Faculty of Forestry. University of British Columbia, Vancouver, Canada. Chapter 3, p. 73-91 (1993).  
T. Teeri; "Crystalline cellulose degradation: new insight into the function of cellobiohydrolases", May 1997, vol. 15, p. 160-167.

* cited by examiner

*Primary Examiner*—Herbert J. Lilling  
(74) *Attorney, Agent, or Firm*—Sughrue Mion, PLLC

(57) ABSTRACT

A process for producing ethanol from a fibrous lignocellulosic raw material. After pre-treatment of the raw material, the fibrous fraction is first hydrolysed at high consistency and then the modified material is subjected simultaneously to continued hydrolysis with a cellulase and to ethanol fermentation in a fermentation mixture. Fermentation is continued to convert an essential portion of the available cellulose into ethanol, then a liquid fraction containing solubilized hemicelluloses is added to the fermentation mixture and fermentation continued. By means of the invention, high fermentation rates, high ethanol concentrations and low ethanol production costs can be attained.

29 Claims, 1 Drawing Sheet

PROCESS FOR PRODUCING ETHANOL

This application is a 371 of PCT/FI2005/000261, filed Jun. 6, 2005; the disclosure of which is incorporated herein by reference.

BACKGROUND OF THE INVENTION

1. Field of the Invention

The present invention relates to the production of ethanol. In particular, the present invention concerns a new process for conversion of fibrous lignocellulosic material to ethanol by fermentation.

2. Description of Related Art

Conversion of biomass to fuel energy has received growing attention as a means of replacing energy derived from fossil fuels. Of the liquid biofuels (ethanol, methanol, fatty acid methyl ester), ethanol has long proven history and environmental advantages. It can be produced from a variety of raw materials. Traditionally, ethanol has been produced from starch or sugar based agricultural products, but today the focus is on different agricultural and forestry residues or side streams from forest industries. A very significant environmental advantage of ethanol production is that there is low generation of $CO_2$, provided that the raw material is driven from renewable waste residues or wood. At present, the cost of ethanol produced from lignocellulose containing raw materials is still too high for several reasons. Among the barriers are the high costs of the lignocellulose conversion technologies, the low concentration and yield of ethanol, as well as the low production rates, which all increase the costs of ethanol produced from lignocellulosics, as compared to ethanol produced from starch or sugar based raw materials.

Conversion of wood or agriculture derived lignocellulosic materials into sugars and further to ethanol is a complex process involving several steps (pretreatment, potential separation of solids, hydrolysis of cellulose, ethanol production from cellulose and hemicellulose and distillation of ethanol). Depending on the raw material, different types of pretreatment techniques are needed. A pretreatment step is usually needed to improve the hydrolyzability of the cellulosic part. The objective of the pretreatment is to render the biomass materials more accessible to either chemical or enzymatic hydrolysis for efficient production of sugars from cellulose and hemicellulose. The goals of the pretreatment are to remove and separate hemicellulose from cellulose, to disrupt and remove the lignin sheath, to decrease the crystallinity of cellulose, to increase the accessible surface area of cellulose, and to increase the pore size of cellulose to facilitate the penetration of hydrolysing agents (Chang and Holtzapple, 2000).

Detailed descriptions of various pretreatment technologies are available (reviewed e.g. by Hsu et al, 1996). Of the various pretreatment options, steam explosion (with sulphuric acid impregnation and with sulfur dioxide) is one of the most extensively studied methods (Chandrakant and Bisaria, 1998).

The maximum digestibility of cellulose usually coincides with complete hemicellulose removal. Therefore, in efficient pretreatment methods, most of the hemicellulose is solubilized and forms a soluble fraction containing mainly hemicellulose derived sugars (referred to as a "hemicellulose filtrate"). The crude hemicellulose filtrate from the pretreatment contains usually various degradation products of lignocellulose. These may be lignin and sugar decomposition products, including furfural, hydroxymethyl furfural and formic and acetic acid. Most of these components are toxic to enzymes and microorganisms slowing the subsequent hydrolysis and fermentation process. A number of different detoxification methods have been investigated (Gong et al. 1999). Neutralization with lime, charcoal treatment and different adsorption resins are among the methods studied. Inhibitors in the hemicellulose filtrate have been shown to severely decrease both the hydrolysis and fermentation rates.

The hydrolysis processes of the cellulosic part may be based either on acid or enzymes. The major disadvantages of the enzymatic hydrolysis are that the process is quite slow and the enzyme costs are still too high (Kaylen et al, 2000). Generally, the hydrolysis yields depend on the type and pretreatment of the substrate, type and dosage of the enzyme and the hydrolysis time. Most experiments have been carried out at low raw material consistencies due to the amount of inhibitory compounds in the substrate derived from the pretreatment stage.

There are essentially two different types of processes that can be used to convert cellulose (and hemicellulose) to ethanol. These are the separate hydrolysis and fermentation (SHF) and the simultaneous saccharification and fermentation (SSF). The latter process has been also extended to contain simultaneous saccharification and hemicellulose fermentation (SSHF), and is also referred as simultaneous saccharification and cofermentation (SSCF). Among various cellulose bioconversion schemes, the SSF seems to be the most promising approach to biochemically convert cellulose to ethanol. Industrial ethanol production is traditionally carried out by yeast, which is a well known robust organism. New strains (either yeasts or bacteria) have been engineered to efficiently utilize all the sugars derived from the lignocellulosic raw material. Utilization of all sugars, including the hemicellulose derived pentoses and all hexoses, is essential for economical production of ethanol.

The hydrolysis conditions used in a separate hydrolysis process (SHF) are determined by the optimum conditions of the enzymes (mostly fungal cellulases having a maximum activity at 50° C. and at a pH in the range from 4 to 5). The main advantage of a separate hydrolysis stage is that the hydrolysis is carried out at the optimum temperature of the enzymes, and the separate fermentation at the optimum of the yeast, about 30° C. The major disadvantage is that the sugars released in the hydrolysis severely inhibit the cellulase activity during hydrolysis. This can be at least partially overcome by increasing the beta-glucosidase activity in the preparation used (by adding separate enzyme or by using an overproducing strain). The cellulase loadings usually range from 10 to 20 FPU/g of substrate (or cellulose), and beta-glucosidase is supplemented. Usually the sugar concentrations produced are quite low due to the low amount of dry matter in the hydrolysis. Yields (from the sugars) are usually higher in more dilute systems, where end product inhibition is minimized. Long reaction times also make higher ethanol yield and concentration possible.

In the simultaneous saccharification and fermentation process (SSF), the saccharification of cellulose to glucose with cellulases and the subsequent fermentation of glucose (and pentoses) to ethanol takes place in the same reactors. According to present process schemes, all reactants (cellulose, enzymes and fermenting organism) have been added at the same time. One of the most important requirements of the SSF process is the compatibility of the saccharification and fermentation systems with respect to temperature (below 37° C.), pH and substrate concentration. The main advantages offered by SSF include enhanced rate of cellulose hydrolysis due to uptake (by yeast) of sugars inhibiting cellulase activity and decreased requirement of aseptic conditions. The disadvantages are the differences in optimal conditions for hydrolysis and fermentation. Using the whole material; both the solid cellulose and hemicellulose filtrate simultaneously for fermentation instead of only the filtrate has shown advantages, for example lactic acid formation is reduced (Stenberg et al. 2000).

SUMMARY OF THE INVENTION

It is an aim of the present invention to improve the economy and efficiency (in terms of raw material utilization) of the known art and to provide a new process for converting lignocellulosic materials into ethanol. In particular, it is an aim of the present invention to increase the final ethanol concentration of fermentation process and to improve production rate and yield.

The invention is based on the idea of operating hydrolysis and fermentation at high substrate concentration and, by avoiding the inhibitory effects of the hemicellulose filtrate, to reduce the amount of enzymes needed and, finally, to decrease the overall ethanol production costs. The few published process configurations (such as the NREL process) have not reached these goals.

The present invention is based on a combination of three main process steps, namely a first step in which the pretreated lignocellulosic material, having an increased concentration of cellulosic or lignocellulosic material capable of being fermented to ethanol, is subjected to a preliminary hydrolysis step at high consistency. Then, hydrolysis is continued during a second step of the invention simultaneously with fermentation. And finally, solubilized hemicelluloses, separated during the pre-treatment of the raw-material, are—potentially after removal of fermentation inhibitors—added to the fermentation mixture and fermentation of the combined substrates is continued to provide increased product yield.

More specifically, the invention is mainly characterized by what is stated in the characterizing part of claim 1.

The present invention comprising the essential features of improved hydrolysis and fermentation technology provides the following advantages:

High hydrolysis rate and high concentration are obtained by starting the hydrolysis at high raw material consistency at the optimal conditions for the prehydrolyzing enzymes End product inhibition is avoided by continuing the main hydrolysis stage simultaneously with ethanol production from the hydrolyzed sugars by the yeast, which consumes the sugars potentially causing end product inhibition of enzymes The amount of enzymes needed is decreased due to reduced end product inhibition and lower need for beta-glucosidase. Concentration and optional detoxification of the hemicellulose fraction improves the ethanol production rate and leads to high final ethanol concentration. Addition of the hemicellulose fraction at later phase reduces the inhibition of enzymes and organisms by any inhibitory compounds. Minimization of inhibitory effects and increasing the raw material (carbohydrate) consistency lead to higher fermentation rates, higher final ethanol concentrations and lower ethanol production costs.

Next the invention will be described in more detail with reference to the attached drawing.

DETAILED DESCRIPTION OF THE INVENTION

Figure 1:
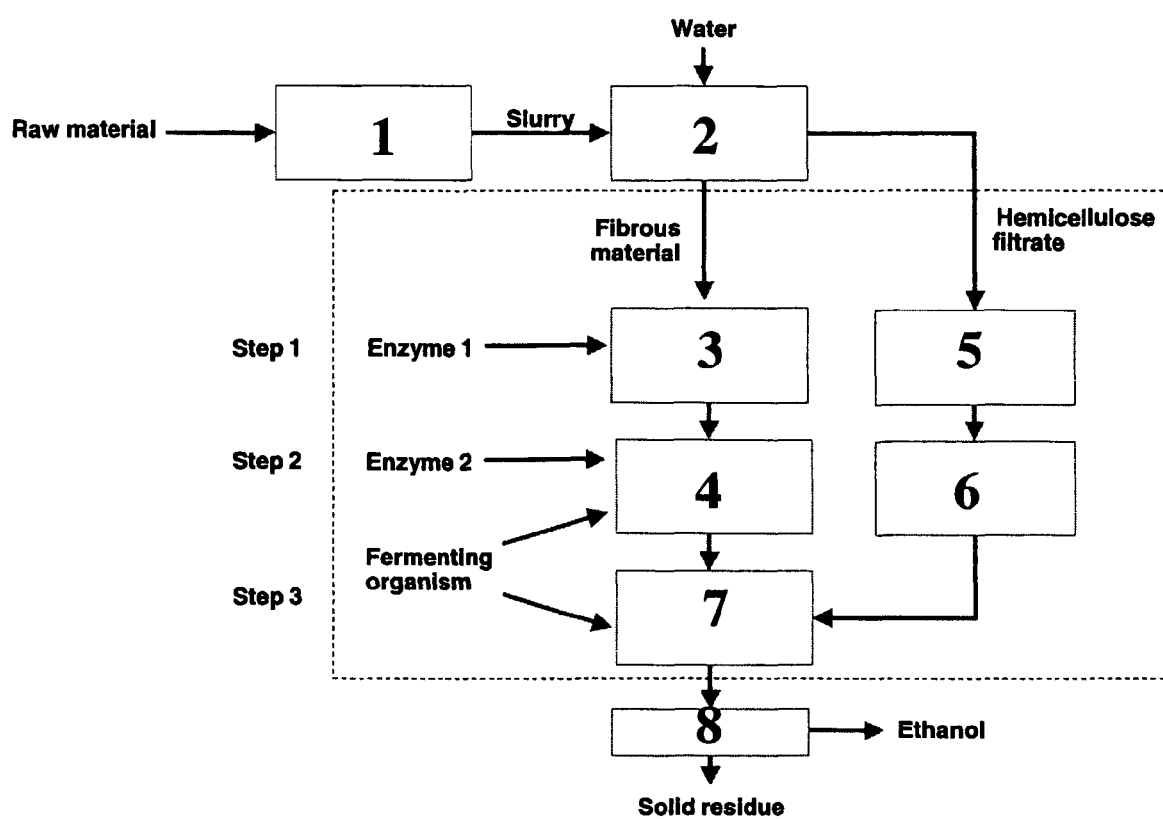
FIG. 1 shows in a schematic fashion the lay-out of a novel three step process according to the invention for converting lignocellulose into ethanol.

The overall process for producing ethanol from a fibrous lignocellulosic raw material, containing carbohydrates, generally comprises the steps of Enzymatic prehydrolysis at high consistency, typically 10% d.w. or more, at optimal temperature of the enzymes. The enzyme composition can be designed specifically for the prehydrolysis or it can be the same during prehydrolysis as in the main hydrolysis stage;

Secondary simultaneous enzymatic main hydrolysis and fermentation of the hexose sugars at temperature suitable for the fermenting organism; and Addition of the concentrated and optionally detoxified hemicellulose fraction after the majority of the hexose sugars have been fermented; this procedure may also allow for the use of a non-detoxified hemicellulose filtrate.

In particular, the process comprises a) converting the raw-material into a solid lignocellulosic fraction with an increased concentration of cellulose and a liquid fraction mainly containing solubilized hemicelluloses;

b) hydrolysing the fibrous lignocellulosic material at high consistency with a cellulose enzyme to provide a modified lignocellulosic material with increased flowability (which stands for, e.g. improved mixing and pumping characteristics), c) simultaneously subjecting the modified lignocellulosic material to continued hydrolysis with a cellulase and to ethanol fermentation in a fermentation mixture, d) continuing fermentation to convert an essential portion of the available carbohydrates into ethanol, e) adding the liquid fraction containing solubilized hemicelluloses to the fermentation mixture and continuing fermentation, and f) recovering ethanol from the fermentation mixture.

In the present process, as a raw material, any lignocellulosic, usually fibrous lingo-cellulosic material, which contains appreciable amounts of cellulose and hemicellulose can be used for ethanol fermentation subject to a hydrolysis of the hydrocarbon material to monomeric sugars, hexoses and pentoses.

Typically, the raw material is selected from softwood and hardwood residues, dedicated crops, agricultural waste, waste paper or a side stream from the forest industry.

Turning now to the drawing it can be noted that the following reference numerals are used for designating the various process steps:

1. Pretreatment
2. Filtration and washing
3. Prehydrolysis
4. Hydrolysis and hexose fermentation
5. Concentration
6. Detoxification
7. Hydrolysis and hemicellulose fermentation
8. Distillation These steps will be examined below:

1. Pretreatment of Raw Material

The raw material is pretreated with a pretreatment method, such as steam explosion, with the aim of releasing hemicelluloses from the lignocellulosic fibrous matrix. As a technique, steam explosion is described in more detail e.g. by Saddler et al. (1993) and an equipment and method for pretreatment is described by Palmqvist et al., (1996).

(Saddler, J, Ramos, L and Breuil, C (1993) Steam pretreatment of lignocellulosic residues. In: Bioconversion of Forest and Agricultural plant Residues. Saddler, J. N. (ed.) CAB International, Wallingford, UK, Chapter 3, 73-92; Palmqvist, E, Hahn-Hägerdal, B, Galbe, M, Larsson, M, Stenberg, K, Szengyel, Z, Tengborg, C and Zacchi, G. 1996 Design and operation of a bench-scale process development unit for the production of ethanol from lignocellulosics. Bioresource Technology 58:171-179)

The raw material comprises lignocellulosic materials such as wood (softwood, hardwood or mixtures thereof) and agriculture derived lignocellulosic materials, such as perennial or annual plants.

2. Filtration and Washing

In the following step, the slurry is subjected to filtration and washing. The fibrous material thus obtained has an increased concentration of cellulose compared to the raw material since a considerable part of the hemicelluloses (about 5 wt-% to 30 wt-% of the total raw material) has been dissolved in liquid phase (aqueous phase). The aim is to separate a considerable part, at least 40 wt-%, in particular at least 50 wt-%, of the hemicelluloses present in the raw material and incorporate them into the liquid phase primarily in monomeric or oligomeric form. Typically, the amount of hemicelluloses/saccharides in the liquid fraction is at least 2-times larger, preferably 2.5 to 15-times larger (calculated by weight), than in the fibrous material.

The filtration is carried out using, e.g., filter presses or other conventional separation methods for the separation and washing of the solids fraction, containing mainly the cellulose. The separation leads to a filter cake (at high temperature) with high solid content and to a liquid fraction containing solubilized hemicelluloses but also the inhibitory compounds.

3. Prehydrolysis (Step b Above)

The hydrolysis of step b is carried out at a temperature of 30-90° C., or 40-90° C., for 0.5 to 24 hours, typically about 1 to 12 hours. The consistency is high, generally from about 5 to 40% dry weight, preferably about 10-25% d.w. or 10-40% dw. The hydrolysis is carried out at slightly acid conditions, preferably at a pH in the range from 4 to 6.

As will be discussed in more detail below, the hydrolysis of step b is carried out at with a first cellulase preparation and the hydrolysis of step c (reference numeral 5 of FIG. 1) is carried out with a second cellulose preparation, the cellulases being either the same or, preferably, different. By using different cellulases it is possible to employ enzymes, which are optimized for their various tasks. Thus, the first enzyme can be specifically optimized for improving the treatability (such as mixing and pumping—generally "flowability") at high consistency, decreasing the viscosity, producing fermentable sugars and being active at temperatures of 30-90° C. in step b. During prehydrolysis, at least some of the cellulose and other carbohydrates will be hydrolysed into sugars (monosaccharides, such as hexoses and pentoses). Typically at least 5%, preferably about 10%-90%, in particular about 20-80%, of the carbohydrates are hydrolysed at this stage to produce fermentable mono-saccharides. In the below examples, the hydrolysis degree has been about 20-70%

Preferably, the enzyme used in step b has a broad spectrum of cellulases. In particular, the enzyme has at least two activities selected from the group consisting of cellobiohydrolase activities, endoglucanase activities, beta-glucosidase activities and hemicellulase activities (cf. below for more detailed explanation of the enzymes).

4. Hydrolysis and Hexose Fermentation

The step of simultaneous hydrolysis and fermentation (step c) is preferably carried out at a temperature in the range of 30 to 70° C. (The hydrolysis of step b is preferably carried out at a higher temperature than the hydrolysis and fermentation of step c). Hydrolysis is continued with a second enzyme, which is active at this temperature for a reaction time of 6 to 96 hours.

The enzyme used in step c has a broad spectrum of cellulases and is active at temperatures of 30 to 90° C. The enzyme has preferably at least two activities selected from the group consisting of cellobiohydrolase activities, endoglucanase activities, beta-glucosidase activities and hemicellulase activities. It is specifically optimized to carry out the hydrolysis of the remaining lignocellulosic material in steps c to e.

The two enzymes are preferably of the same origin and designed for efficient hydrolysis of the lignocellulosic material in the whole process consisting of steps b to e.

A more complete description of the enzymes is given below.

During hydrolysis, the remaining cellulose and other carbohydrate portions of the cellulosic and lignocellulosic material is converted to sugars.

The fermentation step is carried out in the presence of a fermenting organism, capable of fermenting major lignocellulose derived carbohydrates (sugars), i.e monosaccharides, such as hexoses and pentoses. The fermenting organism is capable of producing ethanol from the major lignocellulose derived sugars at temperature of 30-70° C.

Examples of Suitable Organisms are the Following:

Yeasts:
*Saccharomyces cerevisiae*, including genetically modified organisms (GMO), such as VTT strain B-03339
*Pichia stipitis*
*Candida shehatae*
*Hansenula polymorpha*
*Pachysolen tannophilus*
*Brettanomyces naardenensis*
*Pichia segobiensis*
*P. guillermondii*
*P. naganishii*
*Candida tenuis*
*C. albicans*
*C. tropicalis*
*C. maltosa*
*C. torresii*
*Metschnikowia bicuspidata*
*M. zobellii*
*Sporopachydermia quercuum*
*Wingea robertsii*
Bakteria:
*Zymomonas mobilis*
*E. coli* (GMO—kanta/kantoja)
*Klebsiella oxytoca* (GMO—kanta)
Fungi:
*Fusarium oxysporum*
*Candida guillermondii*
*C. millerii*
*C. tropicalis*
*C. parapsilosis*
*Petromyces albertensis*
*Debaromyces hansenii*
*Cellulomonas cellulans*
*Corynebacterium* sp.
*Serratia marcescens*

In particular, the fermenting organism is a yeast, capable of producing ethanol from the major lignocellulose derived sugars.

5. Concentration

The concentration of the liquid fraction obtained from the filtration step is increased after before the liquid is added to the fermentation mixture. Thus, it is preferred to increase the concentration of the hemicellulose fraction to a dry weight concentration of 5-60%.

The concentration can be carried out by evaporation and by various membrane techniques. During concentration by evaporation, some compounds inhibitory to fermenting organisms may also be removed from hemicellulose filtrate.

6. Detoxification

The liquid fraction can be—depending on the conditions of the pre-treatment subjected to a detoxification operation to free the hemicellulose fraction from substances that may inhibit fermentation. The inhibitors can be removed, e.g., by stripping, evaporation, ion exclusion, resin or the charcoal treatment method.

7. Hydrolysis and Hemicellulose Fermentation

The liquid fraction is added when an essential part of the carbohydrate substrate available for fermentation during step c has been fermented to ethanol. Preferably least 50 wt-%, in particular at least 55 wt-% or at least 60 wt-%, of the available monosaccharides, in particular hexoses and pentoses, formed during hydrolysis, are fermented to ethanol before the liquid fraction is added. The concentrated hemicellulose fraction is then added during a time period of 10 minutes to 48 hours, preferably about 15 min to 24 hours, after which time fermentation is continued for a further 6 to 72 hours, preferably 8 to 48 hours, at a temperature of 30-70° C. and a pH of 4 to 6.

As a result of the above process, a fermentation mixture is obtained containing generally about 0.5 to 10%, in particular about 1.5 to 8%, by weight of ethanol. The yield (calculated from the available carbohydrates is 80 wt-% or greater, in particular 85 wt-% or more).

8. Ethanol Distillation

Ethanol distillation and dehydration is carried out with conventional or new techniques.

Cellulolytic Enzymes

The enzymatic hydrolysis steps mentioned above can be carried out with mixtures of cellulase enzymes. The mixtures are composed in particular of the major three types of enzymes: cellobiohydrolases (CBH's), endoglucanases (EG's) and α-glucosidases. In addition, the mixtures may contain other hydrolytic enzymes, such as hemicellulases. The composition of enzyme mixtures is optimised to hydrolyse the carbohydrates, especially cellulose, efficiently to monomeric sugars. For this, cellobiohydrolases are needed to act on crystalline part of cellulose, endoglucanases mainly on amorphous part of cellulose, and beta-glucosidases to remove cellobiose from hydrolysis mixtures because cellobiose inhibits the action of CBH enzymes due to end-product inhibition. The hydrolysis mechanisms are well known and they are described in more detail e.g. by Teeri (1997). The present commercial cellulase enzyme preparations originate mainly from fungi (e.g. *Trichoderma, Aspergillus*). The properties of the mixtures can be improved or made suitable for specific conditions using biotechnical methods. The mixtures can be modified to contain new cellulase proteins derived from other organisms using genetic engineering methods, or the properties of the present cellulase proteins can be improved by protein engineering.

(Teeri, T. (1997) Crystalline cellulose degradation: new insight into the function of cellobiohydrolases. TIBTECH 15 (May 1997), p. 161-167.)

The following non-limiting examples further illustrate the invention:

EXAMPLE 1

Pre-Hydrolysis of Pretreated Softwood

Softwood was steam pretreated and divided into two fractions; a solid fraction containing mainly cellulose and a soluble fraction containing mainly the hemicellulose sugars and the inhibitory compounds. The solid fraction was filtrated, washed and suspended to form a fibre suspension with dry matter of 14.4%. The fibre was pre-hydrolyzed using commercial enzyme preparations (Celluclast 1.5 L FG, 20 FPU/g d.w. and Novozym 188, beta-glucosidase dosage 200 nkat/g d.w) at 50° C. for 2 to 20 hours.

During the hydrolysis 74% of the cellulose of fibre was hydrolysed to glucose that was present in the liquid fraction in the concentration of 46 g/l. In addition, the liquid part contained small amounts of other fermentable sugars: 0.1 g/l mannose, 0.03 g/l galactose and 0.04 g/l xylose. The viscosity of the solid fraction was decreased rapidly during the hydrolysis and the mixing properties were clearly improved already within 2 first hours of hydrolysis, creating more favourable processing characteristics of the fibre suspension.

Steam pre-treated softwood was also directly treated with enzymes, similarly as described earlier, but without separation of hemicellulose sugar fraction and without washing. In this case the hydrolysis rate was only 11% of that obtained with washed fibre (8% of the cellulose of fibre was hydrolysed), indicating that the pre-hydrolysis stage is clearly more efficient in the case the hemicellulose fraction is separated from the fibre prior to pre-hydrolysis.

When the corresponding hydrolysis experiment was carried out with lower fibre content (dry matter of 2%), the hydrolysis rate with unwashed fibre was better: 66% of hydrolysis rate with washed fibre. This indicates that the inhibition of enzymes by hemicellulose filtrate becomes clearly more severe when the content of fibre is increased. Thus the separation of hemicellulose filtrate from the fibre is very important for efficient hydrolysis in prehydrolysis stage in high consistency process.

EXAMPLE 2

Ethanol Production from Prehydrolysed Softwood

Softwood was steam pretreated and divided into two fractions; a solid fraction containing mainly cellulose and a soluble fraction containing mainly the hemicellulose sugars. The solid fraction was filtrated, washed and suspended to form a fibre suspension with dry matter of 14.5%. The fibre was pre-hydrolyzed using commercial enzyme preparations at 50° C. The hydrolysis conditions were: 13.3% solids d.w. in acetate buffer, pH 5, the enzyme preparations used were Celluclast 1.5 L FG, 20 FPU/g d.w. and Novozym 188, with beta-glucosidase dosage 200 nkat/g d.w. After 20 hours, the prehydrolyzate was tempered to 30° C. and inoculated with the yeast (strain VTT-B-03339) suspended with nutrients before inoculation in 10 vol-% (of the pre-hydrolysate) to water. The reference treatment was carried out under the same conditions, but the yeast was inocculated in the beginning of the process immediately after the addition of the enzymes.

The experiment with pre-hydrolysis and the reference treatment both resulted in an ethanol concentration of 25 g/l, corresponding to an ethanol yield of 81% of the theoretical. Thus, the pre-hydrolysis was as good as the separate hydrolysis in terms of ethanol production in the process, and furthermore resulted in better mixing properties with lower energy demand.

EXAMPLE 3

Ethanol Production from Pre-Hydrolysed Softwood With and Without the Hemicellulose Fraction Softwood was steam pre-treated and divided into two fractions; a solid fraction containing mainly cellulose, and a soluble fraction containing mainly the hemicellulose sugars. The solid fraction was filtered, washed and suspended to form a fibre suspension with dry matter of 18%. The fibre was pre-hydrolyzed using commercial enzyme preparations at 50° C. The hydrolysis conditions were: 16.2% solids d.w. in acetate buffer, pH 5, the enzyme preparations used were Celluclast 1.5 L FG, 20 FPU/g d.w. and Novozym 188, with beta-glucosidase dosage 200 nkat/g d.w. After pre-hydrolysis ca. 20% of the cellulose in fibre fraction had been hydrolysed to glucose.

After 20 hours, the prehydrolyzate was tempered to 30° C. and inoculated with the yeast (strain VTT-B-03339) suspended before inoculation with nutrients in ca. 10 vol-% (of the pre-hydrolysate) to water.

The hemicellulose filtrate containing inhibitors and toxic compounds for yeast was added either:
a) in the beginning of the hydrolysis (resulting in 13.3% solids d.w. in hydrolysis).
b) in the beginning of the fermentation at the same time as the yeast, or
c) by two consequent additions after the beginning of the fermentation.

The reference treatment was carried out using the unwashed steam pre-treated material containing the hemicellulose fraction, i.e. the material with no separation of hemicellulose fraction, and with no washing.

The ethanol concentrations produced in the yeast fermentation were in the different cases: a) 0.2%, b) 2.6% and c) 3.2%. The reference treatment produced only 0.15% ethanol. The sugars from the added filtrate were only partially utilized in the case b), whereas the major part of them was consumed in the case c). The results indicate that the gradual addition of the toxic filtrate at the latter stage of the fermentation improved the yields and production rates. Due to the toxicity of the filtrate, both the hydrolysis and the fermentation rates were decreased.

EXAMPLE 4

Removal of Inhibitors from Hemicellulose Filtrate by Evaporation

Hemicellulose filtrate was separated from steam pretreated sprucre fibre and concentrated 4.8 times by vacuum evaporation at 60-65° C. The filtrate was analysed before and after concentration by HPLC for monosaccharides and several inhibitory compounds: acetic acid, furfural and 5-hydroxy methyl furfural (5-HMF).

During evaporation, furfural was removed from the filtrate (the amount being below detection limit of HPLC in the concentrate). In the concentration by evaporation the amount of acetic acid was reduced by 67% and the amount of 5-HMF was reduced by 12%. Thus, the amount of several inhibitory compounds can be reduced or they can be removed from hemicellulose filtrate by evaporation, carried out in order to concentrate the hemicellulose filtrate prior to its addition to the fermentation process.

EXAMPLE 5

Ethanol Production from Pretreated Softwood in a Three-Step Process

The entire process was tested at high solid dry weight consistency (13 w-% in pre-hydrolysis stage) conditions with addition of concentrated hemicellulose fraction (27% sugar concentration) during the later SSF stage. The experiment was carried out in laboratory fermenter with pH and temperature control and efficient mixing of the slurry. The experiment was started at a consistency of 13% with the pre-hydrolysis step at 50° C. (addition of enzyme as described in Example 2) and continued for 24 hours. After pre-hydrolysis, 60% of the cellulose in the fibre fraction had been hydrolysed to glucose.

The temperature of the fermenter was then decreased to 30° C., adequate nutrients were added and the fermentor was inoculated with the pentose-fermenting yeast (strain VTT-B-03339). The sugars produced in the hydrolysis were quickly consumed and the simultaneous hydrolysis and fermentation continued. After 24 hours from the yeast inoculation, the addition of the concentrated hemicellulose fraction, detoxified and concentrated by evaporation (to about 20% of the original volume) was started and continued for about 25 hours.

When the fermentation was completed, the ethanol concentration was 4.5% corresponding to a theoretical yield of ca. 90% of the carbohydrates in the raw material. The major part of the sugars in the filtrate was also utilized: e.g. the overall use of mannose and glucose were 92% and 95%, respectively, of the all mannose or glucose present in the raw materials. The process produced thus a high concentration and yield of ethanol, and facilitated the utilisation of the sugars of the hemicellulose fraction.

The invention claimed is:

1. A process for producing ethanol from a fibrous lignocellulosic raw material, comprising
    a) converting the raw material to a solid lignocellulosic fraction with an increased concentration of cellulose and a liquid fraction mainly containing solubilized hemicelluloses;
    b) hydrolysing the fibrous lignocellulosic material at high consistency with a cellulase enzyme to provide a modified lignocellulosic material with increased flowability;
    c) simultaneously subjecting the modified lignocellulosic material to continued hydrolysis with a cellulase and to ethanol fermentation in a fermentation mixture;
    d) continuing fermentation to convert an essential portion of the available carbohydrates into ethanol;
    e) adding the liquid fraction containing solubilized hemicelluloses to the fermentation mixture and continuing fermentation; and
    f) recovering ethanol from the fermentation mixture.

2. The process according to claim 1, wherein the raw material is subjected to steam-explosion in step a.

3. The process according to claim 1, wherein the hydrolysis of step b is carried out at a temperature of 40-90° C. for 0.5 to 24 hours.

4. The process according to claim 3, wherein the hydrolysis of step b is carried out at a consistency of 10-25% d.w.

5. The process according to claim 3, wherein the hydrolysis of step b is carried out at a pH in the range from 4 to 6.

6. The process according to claim 3, wherein the hydrolysis of step b is carried out at with a first cellulase preparation and the hydrolysis of step c is carried out with a second cellulose preparation, said first and second cellulases being different.

7. The process according to claim 1, wherein the enzyme used in step b has a broad spectrum of cellulases and is active at temperatures in the range of 30 to 90° C.

8. The process according to claim 7, wherein the enzyme has at least two activities selected from the group consisting of cellobiohydrolase activities, endoglucanase activities, beta-glucosidase activities and hemicellulase activities.

9. The process according to claim 1, wherein the hydrolysis of step b is carried out at a higher temperature than the hydrolysis and fermentation of step c.

10. The process according to claim 1, wherein step c is carried out at a temperature in the range of 30 to 70° C.

11. The process according to claim 1, wherein the enzyme used in step c has a broad spectrum of cellulases and is active at temperatures of 30 to 90° C.

12. The process according to claim 11, wherein the enzyme has at least two activities selected from the group consisting of cellobiohydrolase activities, endoglucanase activities, beta-glucosidase activities and hemicellulase activities.

13. The process according to claim 11, wherein the enzyme used in step c is capable of hydrolysing the lignocellulosic material present in steps c to e.

14. The process according to claim 1, wherein the fermentation step is carried out in the presence of a fermenting organism, which is capable of fermenting major lignocellulose derived sugars.

15. The process according to claim 14, wherein the fermenting organism is able to produce ethanol from the major lignocellulose derived sugars at temperature of 30-70° C.

16. The process according to claims 14, wherein the fermenting organism is a yeast, capable of producing ethanol from the major lignocellulose derived sugars.

17. The process according to claim 1, wherein the fermentation is carried out at a temperature of 30-70° C., and hydrolysis is continued with a second enzyme, which is active at this temperature for a reaction time of 6 to 96 hours.

18. The process according to claim 1, wherein the liquid fraction containing dissolved hemicelluloses is added to the fermentation mixture when at least 50 wt-% of the available hexoses and pentoses have been fermented to ethanol.

19. The process according to claim 18, wherein the concentration of the liquid fraction is increased after step a and before step d.

20. The process according to claim 19, wherein hemicellulose fraction is added at a dry weight concentration of 5-60%.

21. The process according to claim 1, wherein the liquid fraction is subjected to a detoxification operation to free the hemicellulose fraction form substances that may inhibit fermentation.

22. The process according to claim 21, wherein the inhibitors are removed by stripping, evaporation, ion exclusion, resin or the charcoal treatment method.

23. The process according to claim 18, wherein the concentrated hemicellulose fraction is added during a time period of 10 minutes to 48 hours, after which time fermentation is continued for a further 6 to 72 hours at a temperature of 30-70° C. and a pH of 4 to 6.

24. The process according to claim 1, wherein the first and the second enzymes are of the same origin and designed for efficient hydrolysis of the lignocellulosic material in the whole process consisting of steps b to e.

25. The process according to claim 1, wherein the lignocellulosic raw material originates from softwood, hardwood, dedicated crops, agricultural waste, waste paper or a side stream from the forest industry.

26. The process according to claim 1, comprising
hydrolysing the fibrous lignocellulosic material at a consistency of 10 to 40% d.w. with a cellulase enzyme to hydrolyse about 20 to 80% of the carbohydrates to provide a modified lignocellulosic material containing hexoses and pentoses, said material having increased flowability;
simultaneously subjecting the modified lignocellulosic material to continued hydrolysis with a cellulase and to ethanol fermentation of the hexoses and pentoses in a fermentation mixture;
adding the liquid fraction containing solubilized hemicelluloses to the fermentation mixture when at least 50 wt-% of the available hexoses and pentoses have been fermented to ethanol and continuing fermentation; and
recovering ethanol from the fermentation mixture.

27. The process according to claim 1, wherein the fibrous lignocellulosic raw material contains carbohydrates.

28. The process according to claim 14, wherein the major lignocellulose derived sugars are monosaccharides.

29. The process according to claim 28, wherein the monosaccharides are selected from the group consisting of hexoses and pentoses.

* * * * *